United States Patent
Kim

(10) Patent No.: US 10,940,268 B2
(45) Date of Patent: Mar. 9, 2021

(54) LIQUID MEDICINE INJECTION APPARATUS CAPABLE OF INJECTING ADDITIONAL FLUID AFTER COMPLETION OF LIQUID MEDICINE INJECTION

(71) Applicant: E-WHA MEDITECH INC., Goyang-si (KR)

(72) Inventor: Young Mu Kim, Gimpo-si (KR)

(73) Assignee: E-WHA MEDITECH INC., Goyang-si (KR)

( * ) Notice: Subject to any disclaimer, the term of this patent is extended or adjusted under 35 U.S.C. 154(b) by 227 days.

(21) Appl. No.: 16/322,388

(22) PCT Filed: Jul. 24, 2017

(86) PCT No.: PCT/KR2017/007928
§ 371 (c)(1),
(2) Date: Jan. 31, 2019

(87) PCT Pub. No.: WO2018/026130
PCT Pub. Date: Feb. 8, 2018

(65) Prior Publication Data
US 2019/0192775 A1    Jun. 27, 2019

(30) Foreign Application Priority Data
Aug. 1, 2016 (KR) .................. 10-2016-0097783

(51) Int. Cl.
*A61M 5/19* (2006.01)
*A61M 5/315* (2006.01)
(Continued)

(52) U.S. Cl.
CPC .............. *A61M 5/19* (2013.01); *A61M 5/178* (2013.01); *A61M 5/2046* (2013.01); *A61M 5/28* (2013.01);
(Continued)

(58) Field of Classification Search
CPC .......... A61M 5/19; A61M 5/315; A61M 5/28; A61M 5/31515; A61M 5/31596;
(Continued)

(56) References Cited

U.S. PATENT DOCUMENTS 6,723,074 B1    4/2004 Halseth
9,238,110 B2    1/2016 Davies et al.
(Continued)

FOREIGN PATENT DOCUMENTS

GB        770341 A      3/1957
JP     2004505681 A     2/2004
(Continued)

OTHER PUBLICATIONS

International Search Report for Corresponding International Application No. PCT/KR2017/007928 (2 Pages) (dated Nov. 6, 2017).
(Continued)

*Primary Examiner* — Bradley J Osinski
(74) *Attorney, Agent, or Firm* — Lucas & Mercanti, LLP

(57) ABSTRACT

A liquid medicine injection apparatus capable of injecting an additional fluid after completion of injection of a liquid medicine is provided. The apparatus includes a cylinder elongated in a direction and having a nozzle formed at one end of the cylinder; a piston installed to be hermetically movable within the cylinder in the direction; an injector provided at the other end of the cylinder to allow the piston to be moved; a fluid tank for storing a fluid in a sealed state; a needle unit disposed between the nozzle and the fluid tank; and a cap member provided between the needle unit and the fluid tank and deformable to allow the needle unit to penetrate the fluid tank.

13 Claims, 12 Drawing Sheets

(51) Int. Cl.
*A61M 5/28* (2006.01)
*A61M 5/178* (2006.01)
*A61M 5/20* (2006.01)
*A61M 5/31* (2006.01)
*A61M 5/32* (2006.01)

(52) U.S. Cl.
CPC .......... *A61M 5/315* (2013.01); *A61M 5/3146* (2013.01); *A61M 5/31515* (2013.01); *A61M 5/31596* (2013.01); *A61M 5/3202* (2013.01); *A61M 5/3286* (2013.01); *A61M 5/3294* (2013.01); *A61M 2005/1787* (2013.01); *A61M 2005/3128* (2013.01)

(58) Field of Classification Search
CPC ........ A61M 5/3294; A61M 2005/1787; A61M 2005/3128; A61M 5/14526; A61M 5/284
See application file for complete search history.

(56) References Cited

U.S. PATENT DOCUMENTS

| | | |
|---|---|---|
| 2004/0138611 A1 | 7/2004 | Griffiths et al. |
| 2013/0237922 A1 | 9/2013 | Davies et al. |
| 2015/0032063 A1 | 1/2015 | Thorne |

FOREIGN PATENT DOCUMENTS

| | | |
|---|---|---|
| JP | 2005027805 A | 2/2005 |
| JP | 2015112211 A | 6/2015 |
| KR | 20-0234119 Y1 | 9/2001 |
| KR | 10-0507593 B1 | 8/2005 |
| KR | 10-1121082 B1 | 3/2012 |
| KR | 10-1377987 B1 | 3/2014 |
| KR | 10-1397129 B1 | 5/2014 |
| WO | 0211791 A1 | 2/2002 |
| WO | 03066138 A1 | 8/2003 |

OTHER PUBLICATIONS

European Search Report for EP17837182.9, dated Dec. 11, 2019.

LIQUID MEDICINE INJECTION APPARATUS CAPABLE OF INJECTING ADDITIONAL FLUID AFTER COMPLETION OF LIQUID MEDICINE INJECTION

CROSS-REFERENCE TO RELATED APPLICATIONS

This application is a 371 of PCT/KR2017/007928, filed Jul. 24, 2017 which claims the benefit of Korean Patent Application No. 10-2016-0097783, filed Aug. 1, 2016 the contents of each of which are incorporated herein by reference.

TECHNICAL FIELD

The present invention relates to a liquid medicine injection apparatus capable of injecting an additional fluid after completion of injection of a liquid medicine, and more particularly, to a liquid medicine injection apparatus capable of successively injecting a second liquid medicine after a first liquid medicine has been injected into a patient's body or capable of performing flushing by using an additional fluid such that no liquid medicine remains in the apparatus and/or a tube after the liquid medicine has been injected into the patient's body.

For example, the present invention relates to a liquid medicine injection apparatus implemented as a single apparatus capable of performing a function of successively injecting a second liquid medicine after completion of injection of a first liquid medicine in a case where two kinds of liquid medicines are sequentially administered to a patient in order to enhance a curative effect.

Further, the present invention relates to a liquid medicine injection apparatus capable of performing flushing by using an additional fluid to effectively remove a liquid medicine that may remain in the apparatus and/or a tube after the liquid medicine has been injected into a patient's body.

BACKGROUND ART

When a liquid medicine of special injectable drugs such as anticancer drugs, analgesics and antibiotics is injected into a patient's body, a constant amount of liquid medicine should be continuously injected for a considerably long period of time depending on a patient's condition. If the special injectable drugs are not injected continuously and consistently to meet an amount required by a patient, there is concern that a shock occurs, leading to a medical accident. In view of such a problem, there has been devised and used an automatic injection apparatus for injecting a predetermined amount of liquid medicine per unit time into a patient's body.

As for automatic injection apparatuses for continuously injecting a certain amount of anticancer drugs or analgesics containing a narcotic component into a patient's body, there are a mechanical injection apparatus for pushing out a liquid medicine by gradually moving a plunger of a syringe forward by means of a driving force of a motor, a balloon-type injection apparatus for gradually pushing out a liquid medicine accommodated therein by means of an elastic restoring force, a gas-generation type injection apparatus (see Korean Patent No. 10-0507593) for pushing out a liquid medicine by gradually moving a piston forward by means of a gas at a certain pressure, and the like.

In both existing manual and automatic liquid medicine injection apparatuses, however, a small amount of anticancer drugs or analgesics containing a narcotic component may remain in the apparatuses and/or tubes after the injection of the liquid medicine such as the anticancer drugs or the analgesics containing a narcotic component. If the liquid medicine injection apparatuses and/or the tubes with the remaining liquid medicine therein are discarded, environmental problems may occur and there may also be a problem of collection of a small amount of remaining liquid medicine so that the collected liquid medicine may be illegally distributed. Therefore, after the injection of the anticancer drugs or the analgesics into the patient's body is completed, it is necessary to effectively remove the liquid medicine which may remain in the liquid medicine injection apparatuses and/or the tubes.

In addition, chemotherapy using anticancer drugs may be used solely or in combination with other cancer treatment methods. In order to enhance the effect of a cancer treatment, the chemotherapy may be performed after cancer surgery, and the cancer surgery may be done after the chemotherapy and radiation therapy are performed together. Moreover, in the chemotherapy, one kind of anticancer drug may be administered but two or more kinds of anticancer drugs may be administered to enhance a therapeutic effect, which is often referred to as combination chemotherapy.

For example, FP combination chemotherapy using both 5-fluorouracil and cisplatin has been known as one of effective treatment methods. It has been reported that when 5-fluorouracil and cisplatin are sequentially injected according to the FP combination chemotherapy, the effect of a cancer treatment is enhanced.

However, when two kinds of liquid medicines are jointly administered to a patient in accordance with the combination chemotherapy, injection of a first liquid medicine performed by one liquid medicine injection apparatus is completed and then a separate liquid medicine injection apparatus for injecting a second liquid medicine should be connected to administer the second liquid medicine. Therefore, there is inconvenience that two kinds of liquid medicines cannot be injected by using one apparatus. Accordingly, in order to solve such inconvenience, there is a need for a technique capable of sequentially injecting two kinds of liquid medicines in one apparatus.

SUMMARY

Accordingly, an object of the present invention is to provide a liquid medicine injection apparatus capable of injecting an additional fluid after completion of injection of a liquid medicine.

Specifically, an object of the present invention is to provide a liquid medicine injection apparatus capable of successively injecting a second liquid medicine after a first liquid medicine has been injected into a patient's body or capable of performing flushing by using an additional fluid such that no liquid medicine remains in the apparatus and/or a tube after the liquid medicine has been injected into the patient's body.

For example, the object of the present invention is to provide a liquid medicine injection apparatus implemented as a single apparatus capable of performing a function of successively injecting a second liquid medicine after completion of injection of a first liquid medicine in a case where two kinds of liquid medicines are sequentially administered to a patient in order to enhance a curative effect.

In addition, another object of the present invention is to provide a liquid medicine injection apparatus capable of performing flushing by using an additional fluid to effectively remove a liquid medicine that may remain in the apparatus and/or a tube after the liquid medicine has been injected into a patient's body.

However, these objects are illustrative and do not limit the scope of the present invention.

According to an aspect of the present invention, there is provided a liquid medicine injection apparatus capable of injecting an additional fluid after completion of injection of a liquid medicine, including:

a cylinder elongated in a direction and having a nozzle formed at one end of the cylinder;

a piston installed to be hermetically movable within the cylinder in the direction, wherein the piston defines a liquid medicine storage space to be filled with the liquid medicine introduced through the nozzle;

an injector provided at the other end of the cylinder to allow the piston to be moved forward;

a fluid tank for storing a fluid in a sealed state, wherein the fluid tank is disposed in the cylinder so as to be movable together with the piston and is deformable by a pressure;

a needle unit disposed between the nozzle and the fluid tank, wherein the needle unit can penetrate a portion of the fluid tank to communicate the nozzle with the fluid tank; and a cap member disposed between the needle unit and the fluid tank, wherein before the injection of the liquid medicine with which the liquid medicine storage space is filled is completed, the cap member maintains its shape, whereas after the injection of the liquid medicine with which the liquid medicine storage space is filled is completed, the cap member is deformed to allow the needle unit to penetrate the fluid tank.

Here, after the injection of the liquid medicine is completed, a predetermined pressure corresponding to an excess pressure, by which a pressure generated by the injector exceeds a pressure in the liquid medicine storage space, is exerted on the cap member to deform the cap member, and the predetermined pressure is also exerted on the fluid tank to deform the fluid tank. At this time, the predetermined pressure may be a pressure higher than a pressure necessary for the liquid medicine injection apparatus to inject the liquid medicine into a patient's body through the nozzle.

In the liquid medicine injection apparatus capable of injecting an additional fluid after completion of injection of a liquid medicine according to one embodiment of the present invention, the fluid tank may be installed within the piston. Moreover, the liquid medicine injection apparatus may further include a pressure plate installed to be movable in the piston, wherein the pressure plate is brought into contact with the fluid tank to cause an internal space of the piston with the fluid tank installed therein to be separated from an external space. This pressure plate serves to protect the fluid tank and to uniformly transmit the pressure caused by the injector to a rear surface of the piston.

In the liquid medicine injection apparatus capable of injecting an additional fluid after completion of injection of a liquid medicine according to the embodiment of the present invention, a portion of the fluid tank placed radially with respect to the direction may be formed of a bellows.

In the liquid medicine injection apparatus capable of injecting an additional fluid after completion of injection of a liquid medicine according to the embodiment of the present invention, the needle unit may include a nozzle cap for surrounding the nozzle formed to extend into the liquid medicine storage space; and a needle secured to the nozzle cap.

In the liquid medicine injection apparatus capable of injecting an additional fluid after completion of injection of a liquid medicine according to the embodiment of the present invention, the cap member may surround the nozzle cap, and a portion of the cap member placed radially with respect to the direction and adjacent to the needle may be formed of a bellows.

In the liquid medicine injection apparatus capable of injecting an additional fluid after completion of injection of a liquid medicine according to the embodiment of the present invention, the injector may include a gas generator for generating a gas to press the piston.

In the liquid medicine injection apparatus capable of injecting an additional fluid after completion of injection of a liquid medicine according to the embodiment of the present invention, the fluid may be a liquid medicine different from the liquid medicine with which the liquid medicine storage space is filled, or a flushing fluid, for example, a saline solution.

Advantageous Effects

According to the present invention configured as such, a function of successively injecting a second liquid medicine after completion of injection of a first liquid medicine can be implemented in a single apparatus. That is, according to the present invention, two kinds of liquid medicines can be sequentially injected by one apparatus, thereby solving inconvenience in prior arts in which when two kinds of liquid medicines are required to be jointly administered as in the combination chemotherapy, the two kinds of liquid medicines cannot be injected by using one apparatus.

Furthermore, according to the present invention, when the injection of the liquid medicine is just completed, the fluid tank positioned at the front of the cylinder can be penetrated by the needle unit and the fluid in the fluid tank can be discharged to the tube (not shown) through the needle unit and the nozzle, thereby effectively washing away the liquid medicine remaining in the apparatus and/or in the tube. With this operation, the liquid medicine does not remain in the apparatus and/or in tube after the injection of the liquid medicine into the patient's body is completed, and thus, the present invention can solve problems due to the residual liquid medicine in the apparatus and/or the tube, for example, environmental problems and illegal distribution of dangerous drugs.

Of course, the scope of the present is not limited by the aforementioned effects.

DETAILED DESCRIPTION

Hereinafter, preferred embodiments according to the present invention will be described in detail with reference to the accompanying drawings. The following embodiments of the present invention are just to implement the present invention and are not intended to limit or restrict the scope of the present invention. Thus, those that can be easily contemplated by persons skilled in the art from the detailed description and examples of the present invention are interpreted to fall within the scope of the present invention. References cited herein are incorporated herein by reference.

Figure 1:
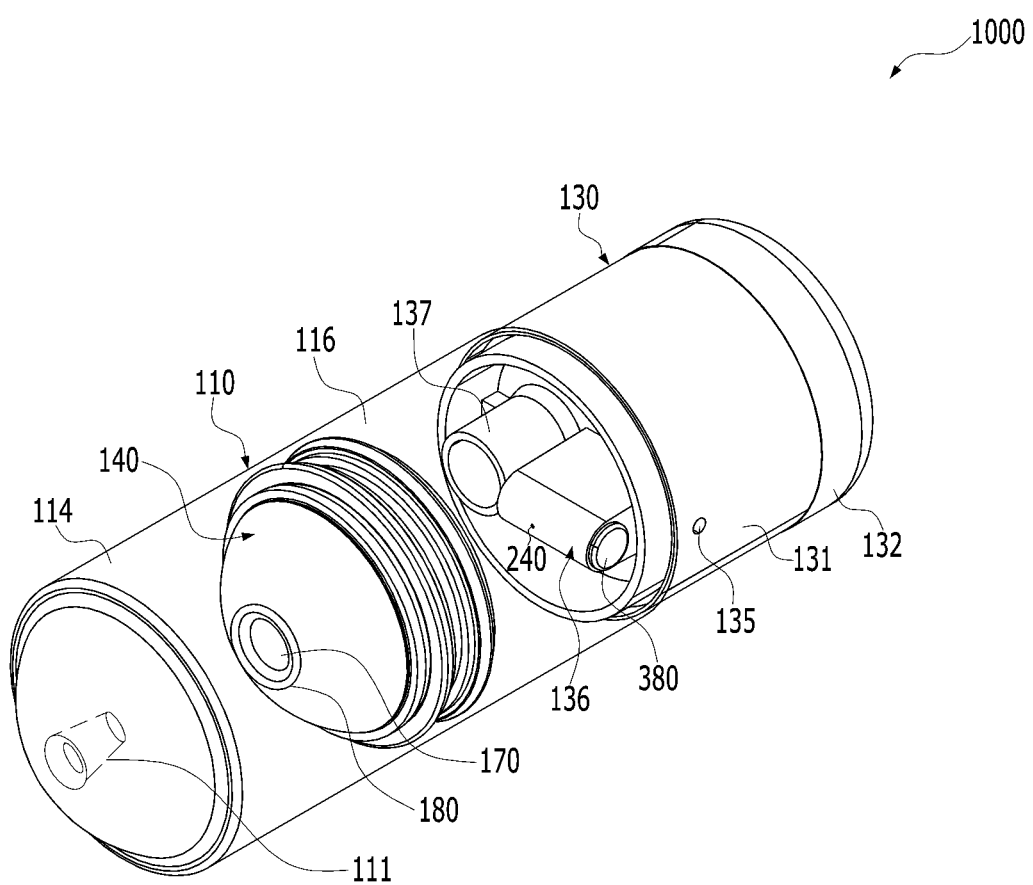
FIG. 1 is a perspective view schematically illustrating a liquid medicine injection apparatus capable of injecting an additional fluid after completion of injection of a liquid medicine according to one embodiment of the present invention.
Figure 2:
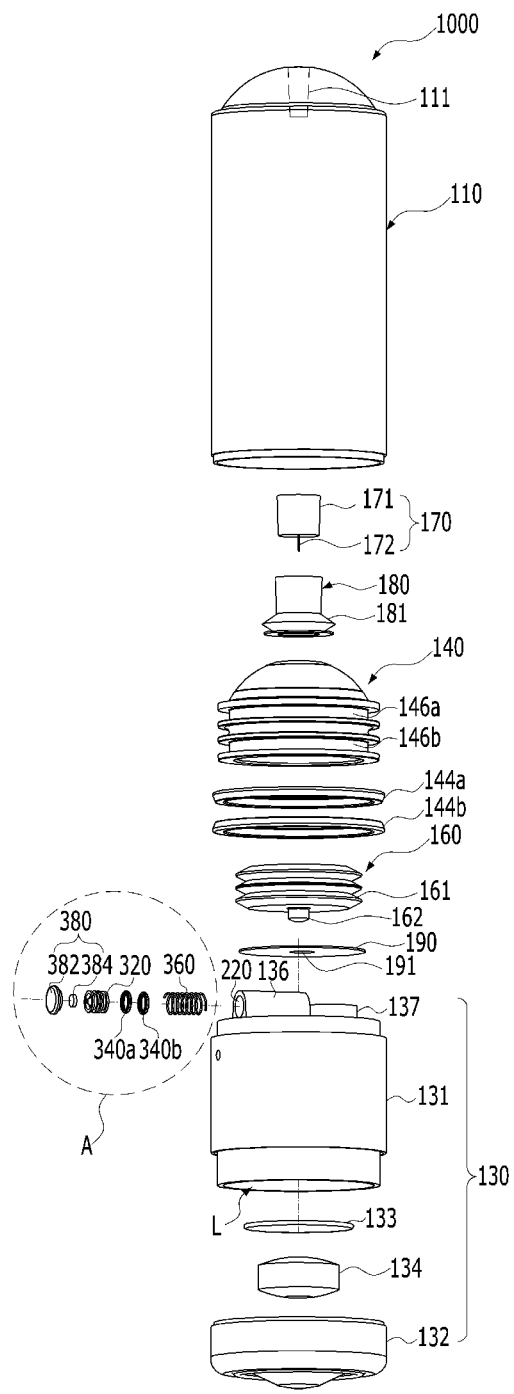
FIG. 2 is an exploded perspective view schematically illustrating the liquid medicine injection apparatus capable of injecting an additional fluid after completion of injection of a liquid medicine according to one embodiment of the present invention.

First of all, as shown in FIGS. 1 and 2, a liquid medicine injection apparatus 100 capable of injecting an additional fluid after completion of injection of a liquid medicine according to this embodiment includes a cylinder 110, a piston 140, an injector, a fluid tank 160, a needle unit 170 and a cap member 180.

As shown in FIG. 1, the cylinder 110 is elongated in a direction and has a nozzle 111 formed at one end of the cylinder. More specifically, the cylinder 110 is formed in a generally cylindrical shape and its end at which the nozzle 111 is formed is curved to be generally convex outwardly. The nozzle 111 is formed at a central region of the end of the cylinder 110. One end of a tube (not shown) is inserted into and coupled to the nozzle 111. An end cap (not shown) may be provided at the other end of the tube (not shown), and an injection needle or a catheter (not shown) may be connected to the end cap.

Here, the nozzle 111 may extend in the shape of a truncated cone in direction toward an inside of the cylinder 110. Of course, the nozzle is not limited thereto.

Furthermore, the cylinder 110 is provided with the injector installed at the other end of the cylinder so as to move the piston 140. Any injector may be used without limitation so far as it has a configuration capable of moving a piston in a manual injection apparatus or an automatic injection apparatus, for example, a mechanical injection apparatus, a balloon type injection apparatus or a gas-generating type injection apparatus. Hereinafter, the injector will be described in connection with the gas-generating type injection apparatus, although it is not limited thereto. A detailed description of the injector will be made later.

The piston 140 is hermetically movable within the cylinder 110 in a direction and can define a liquid medicine storage space 114 in an internal space of the cylinder, wherein the liquid medicine storage space is filled with a liquid medicine introduced through the nozzle 111. In addition, the piston 140 defines a gas-supplied space 116 to which a gas generated in a gas-generating unit 130 to be described later is supplied.

As shown in FIG. 2, sealing ring insertion grooves 146a and 146b are formed between ring-shaped protrusions on a circumference of the piston 140, and sealing rings 144a and 144b are fitted into and coupled to the sealing ring insertion grooves 146a and 146b, respectively. The piston 140 can be hermetically moved within the cylinder 110 by these sealing rings 144a and 144b.

As shown in FIGS. 1 and 2, the gas-generating unit 130 is largely composed of a body part 131 and a cap part 132. The gas-generating unit 130 accommodates a liquid material L and a solid material 134, wherein the liquid material L is accommodated in the body part 131 and the solid material is accommodated in the cap part 132. The solid material 134 is separated from the liquid material L by a partition wall 133 and is accommodated in the cap part 132. The solid material 134 may be pellets including sodium carbonate ($Na_2CO_3$) as a main component and the liquid material L may be an acidic liquid material such as citric acid that generates carbon dioxide upon reaction thereof with the solid material 134.

The liquid material L is accommodated by a gas permeable/liquid impermeable filter (not shown) provided on a circumference and a bottom of the body part 131, and the liquid material L does not flow into the gas-supplied space 116 of the cylinder 110 due to a liquid sealing function of this filter. When the partition wall 133 is detached due to an external force exerted on the cap part 132 and the solid material 134 falls into the body part 131, the solid material reacts with the liquid material L to generate a gas, i.e., carbon dioxide. The generated gas passes through the gas permeable/liquid impermeable filter in the body part 131 and is discharged into the gas-supplied space 116 of the cylinder 110, thereby pushing a rear portion of the piston 140. A boss 137 protruding from the body part 131 of the gas-generating unit 130 may be provided with a pressure regulating valve (not shown) for preventing the pressure of the gas from exceeding a pre-set pressure.

Meanwhile, since the cylinder 110, the piston 140, the gas-generating unit 130, the boss 137 and the like are disclosed in prior arts including Korean Patent No. 10-0507593 and may be easily applied to the present invention and configured by those skilled in the art, detailed descriptions of these elements will be omitted.

According to one embodiment of the present invention, a function of successively injecting a second liquid medicine after completion of injection of a first liquid medicine can be implemented in a single apparatus. In other words, according to one embodiment of the present invention, when two kinds of liquid medicines are administered jointly as in combination chemotherapy, the two kinds of liquid medicines can be sequentially injected by means of a single apparatus. Conventionally, after completion of injection of anticancer drugs or analgesics, a small amount of the anticancer drugs or the analgesics remains in the cylinder 110 and/or in a tube (not shown) inserted in and connected to the nozzle 111. However, according to one embodiment of the present invention, it is possible to remove a liquid medicine remaining in the tube and the like, and simultaneously to inject the remaining liquid medicine into a patient's body by means of flushing the tube and the like using a fluid such as a saline solution. A configuration for this operation will be described in detail below.

Referring to FIGS. 1 to 4, the fluid tank 160 can store a fluid in a hermitic state, is movably disposed within the cylinder 110 and is deformable by a pressure of the injector. This fluid tank 160 may be made of a flexible plastic material.

More specifically, since the fluid tank 160 is sealed in a state where the fluid is stored therein, the fluid tank is not deformed even though a considerable pressure is exerted thereon by the injector. However, when a needle 172 to be described later penetrates the fluid tank 160, the fluid tank 160 is deformed to discharge the fluid stored therein. At this time, a pressure at which the fluid tank 160 is deformed may be higher than that required to inject the liquid medicine into the patient's body.

Here, the fluid may be a second liquid medicine different from the first liquid medicine with which the liquid medicine storage space 114 is filled. For example, in case of combination chemotherapy, the fluid may be another anticancer drug that is used jointly with the first liquid medicine that is an anticancer drug. However, it is apparent that the fluid in the present invention is not limited thereto.

Moreover, the fluid may be a flushing fluid, for example, a saline solution. Of course, the fluid is not limited thereto and may be composed of a substance that does not affect a human body upon injection thereof.

The fluid tank 160 will be described in greater detail. The fluid tank 160 generally has a cylindrical shape. More specifically, two flat circular plates are spaced apart from each other generally in parallel. Here, the two circular plates will be described as an upper plate and a lower plate.

The needle 172 penetrates the upper plate of the fluid tank 160. In other words, when the upper plate is disposed within the piston 140 as described below, the upper plate is disposed on the side of the nozzle 111.

The lower plate of the fluid tank 160 includes a receiving portion 162 for receiving the needle 172 when the needle 172 completely penetrates the fluid tank. The receiving portion 162 protrudes outwardly from the fluid tank 160 and is generally formed to have a cup shape such that a hollow is defined therein.

Figure 3:
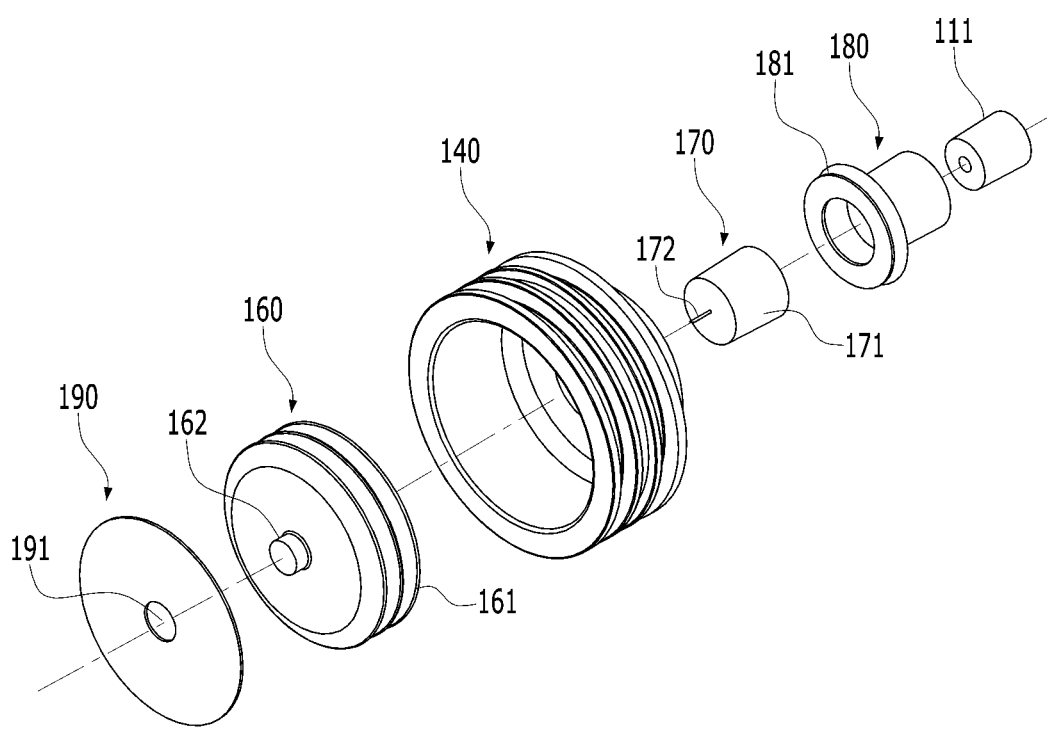
FIG. 3 is an exploded perspective view schematically illustrating a portion of the liquid medicine injection apparatus capable of injecting an additional fluid after completion of injection of a liquid medicine according to one embodiment of the present invention.
Figure 4:
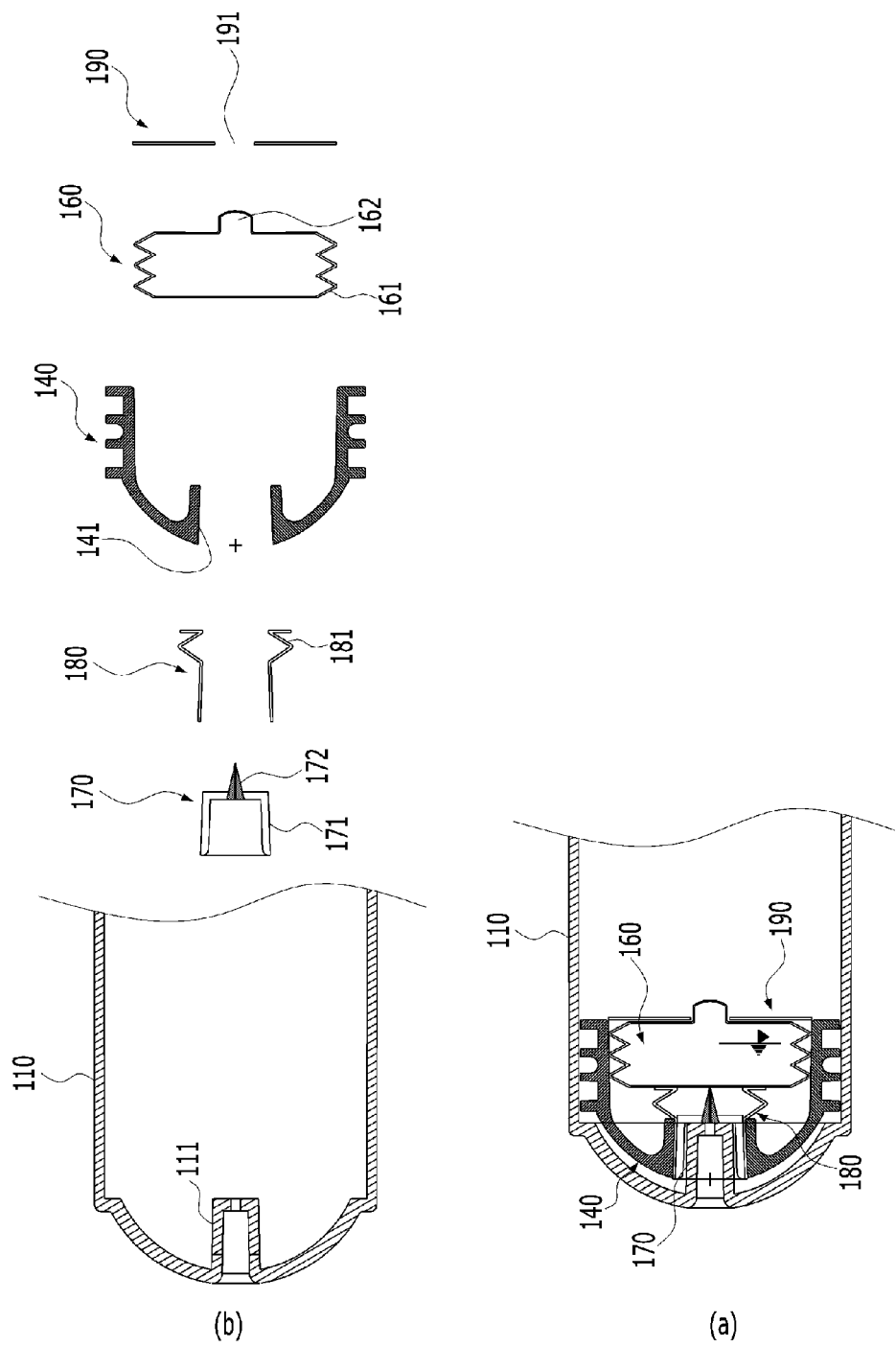
FIG. 4 is a sectional view schematically illustrating a portion of the liquid medicine injection apparatus capable of injecting an additional fluid after completion of injection of a liquid medicine according to one embodiment of the present invention.
Figure 5:
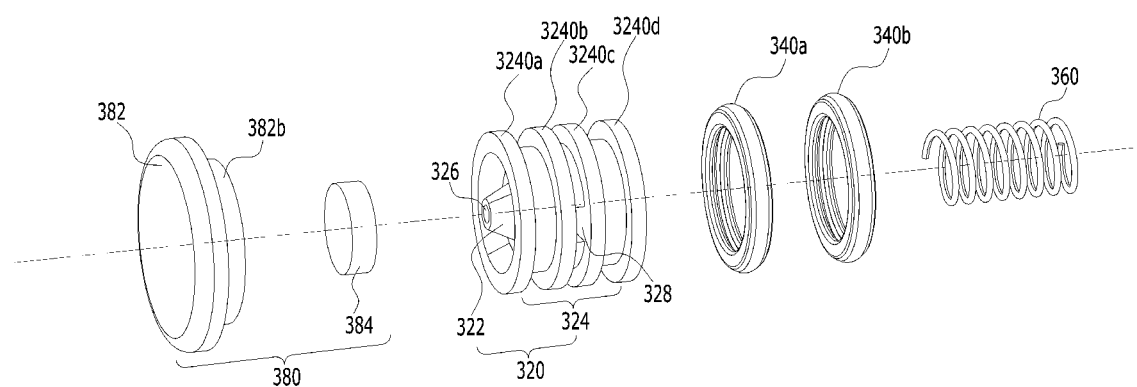
FIG. 5 is an exploded perspective view schematically illustrating a portion of a liquid medicine injection apparatus capable of injecting an additional fluid after completion of injection of a liquid medicine according to another embodiment of the present invention.
Figure 6:
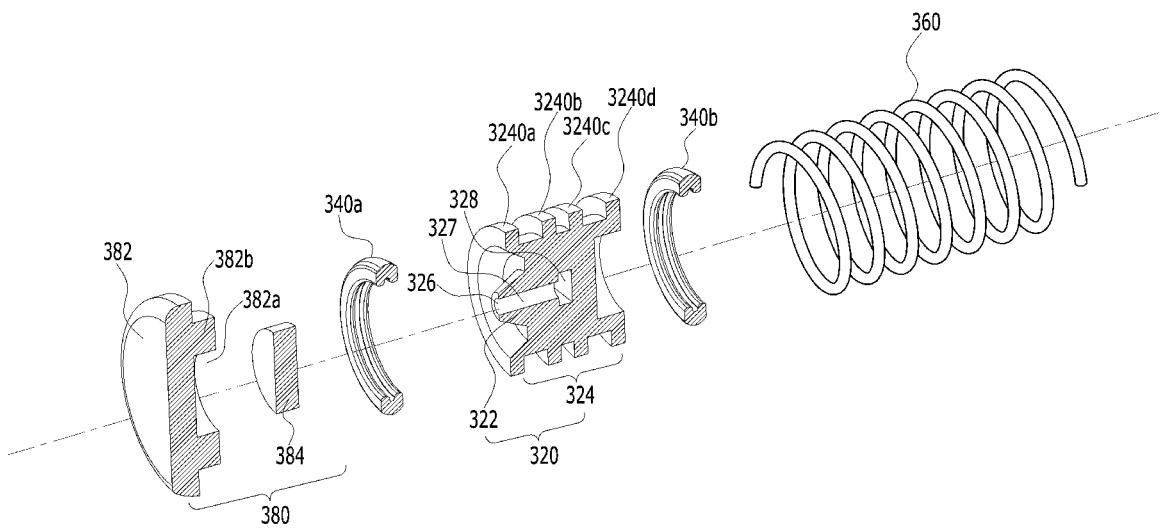
FIG. 6 is a sectional view schematically illustrating a portion of the liquid medicine injection apparatus capable of injecting an additional fluid after completion of injection of a liquid medicine according to another embodiment of the present invention.
Figure 7:
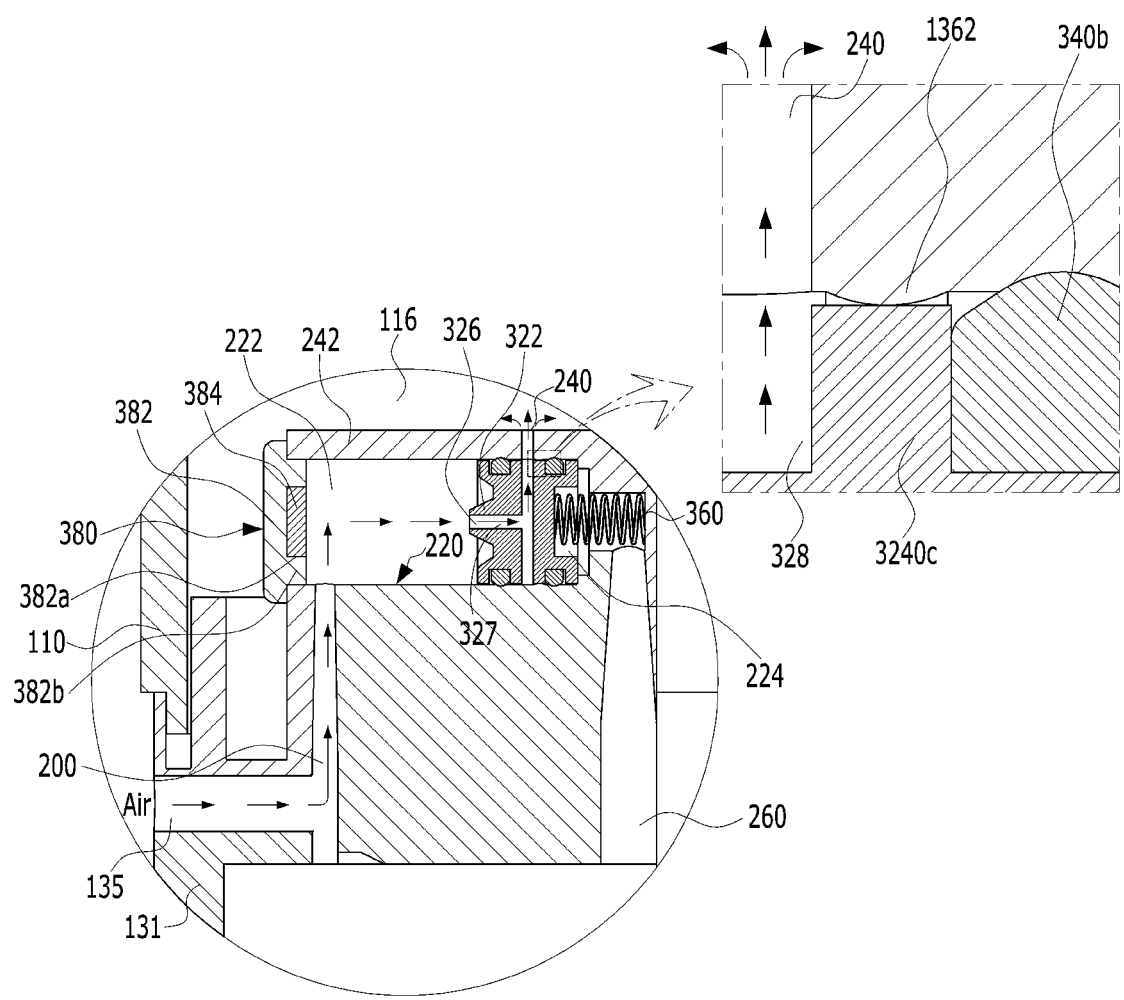
FIG. 7 is a sectional view schematically illustrating a portion of the liquid medicine injection apparatus capable of injecting an additional fluid after completion of injection of a liquid medicine according to another embodiment of the present invention.
Figure 8:
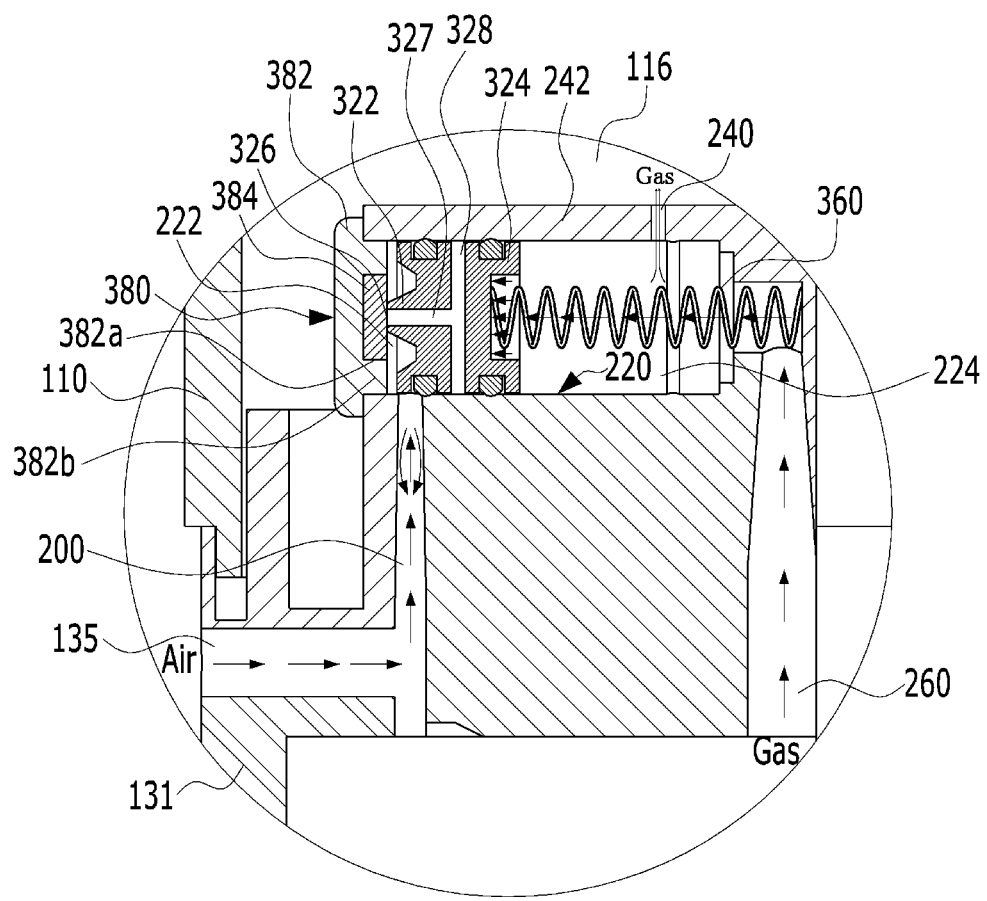
FIG. 8 is a sectional view schematically illustrating a portion of the liquid medicine injection apparatus capable of injecting an additional fluid after completion of injection of a liquid medicine according to another embodiment of the present invention.

The fluid tank 160 includes a side portion connecting the upper plate and the lower plate. Here, the side portion of the fluid tank 160 may be deformed when it is subjected to a pressure. At this time, the fluid tank includes a bellows 161 to be easily deformed, to be linearly deformed or to allow for prediction of a deformation direction. When the fluid tank 160 is installed in the cylinder 110, for example, a portion of the fluid tank 160 which is disposed radially with respect to the direction, i.e., the side portion, may be formed of a bellows 161. As shown in FIGS. 3 and 4, the fluid tank 160 is formed of two opposite flat circular plates and the bellows 161 connecting these plates but is not limited thereto.

Thus, when the fluid tank 160 is pierced by the needle 172 to be described below and directly or indirectly subjected to a pressure by the injector, the fluid tank 160 may discharge the fluid stored therein through the needle 172.

This fluid tank 130 may be installed within the piston 140. For example, the inside of the piston 140 is empty, one end of the piston on the side of the nozzle 111 is closed and the other end is opened. The fluid tank 160 may be inserted into the piston 140 via the opened end of the piston 140.

At this time, surfaces of the flat circular plates of the fluid tank 160 are arranged approximately perpendicular to the direction, and the side portion of the fluid tank 160 formed of the bellows 161 is radially disposed with respect to the direction. Thus, the fluid tank 160 can be moved together with the piston 140 by the injector.

The needle unit 170 is disposed between the nozzle 111 and the fluid tank 160, and can penetrate the fluid tank 160 to communicate the nozzle 111 and the fluid tank 160 with each other. More specifically, the needle unit 170 includes a nozzle cap 171 capable of surrounding the nozzle 111 that extends into the liquid medicine storage space 114, and the needle 172 secured to the nozzle cap 171.

The nozzle cap 171 is in the shape of a cup. That is, the nozzle cap 171 is generally formed to have a truncated conical shape and configured such that one end of the nozzle cap is opened and the other end thereof is closed. At this time, the needle 172 is fixed to a central region of the closed end of the nozzle cap 171. The nozzle 111 can be inserted into the opened end of the nozzle cap 171.

The needle 172 may be in the shape of a tube to communicate the inside and the outside of the nozzle cap 171 with each other. The needle 172 may be formed to have a sharpened end to penetrate the fluid tank 160. Therefore, the fluid (for example, a second liquid medicine or a saline solution) stored in the fluid tank 160 can flow into the nozzle 111 along the inside of the needle 171 that has penetrated the fluid tank 160.

The fluid tank 160 is required to maintain its configuration such that the fluid and the liquid medicine are not mixed with each other when the liquid medicine stored in the cylinder 110 is injected into the patient's body. Furthermore, the fluid tank 160 is required to discharge the stored fluid (a second liquid medicine or a saline solution) after the injection of the first liquid medicine into the patient's body is completed. Thus, the needle 172 penetrates the fluid tank 160 after the injection of the liquid medicine into the patient's body is completed.

In order to cause the needle 172 to selectively penetrate the fluid tank 160 as such, the cap member 180 is provided between the needle unit 170 and the fluid tank 160. The cap member 180 maintains a predetermined gap between the needle unit and the fluid tank so that the needle unit 170 may not penetrate a portion of the fluid tank 160, and the cap member is deformed such that the needle unit 170 penetrates the fluid tank 160 when a pressure that is not less than a predetermined pressure is exerted on the cap member. Here, the predetermined pressure may be a pressure corresponding to an excess pressure, by which a pressure generated by the injector (for example, a pressure in the gas-supplied space 116) exceeds a pressure in the liquid medicine storage space 114, or may be a pressure higher than a pressure necessary for the liquid medicine injection apparatus 1000 to inject the liquid medicine into the patient's body through the nozzle 111.

In other words, before the predetermined pressure is exerted on the cap member by the injector (i.e., before completion of the injection of the first liquid medicine), the cap member 180 is not deformed to maintain the predetermined gap, thereby keeping the needle 172 from penetrating the fluid tank 160. When the predetermined pressure is exerted on the cap member 180 (i.e., after completion of the injection of the first liquid medicine), the cap member 180 is deformed to expose the needle 172, thereby causing the needle 172 to penetrate the fluid tank 160.

For example, the cap member 180 may house the nozzle cap 171 and the needle 172 therein. In other words, the cap member 180 is generally formed to be in the shape of a cup slightly larger than the nozzle cap 171. Therefore, while the injection of the liquid medicine is initiated or the liquid medicine is being injected, the cap member 180 accommodates the needle unit 170 such that the needle 172 is not exposed, i.e., the needle 172 does not come into contact with the fluid tank 160.

A portion of the cap member 180 surrounding the needle 172 is formed of a bellows 181 so as to be stably deformed when the predetermined pressure is exerted thereon. More specifically, a portion of a surface of the cap member 180 placed radially with respect to the direction, which is a portion of the cap member 180 adjacent to the needle 172 when the cap member 180 is disposed in the cylinder 110, is formed of the bellows 181. The aforementioned predetermined pressure is a pressure at which the bellows 181 of the cap member 180 is deformed.

Meanwhile, even when the fluid tank 160 is disposed in the internal space of the piston 140, a portion of the fluid tank may be exposed to an outside, for example, to the gas-supplied space 116. At this time, the fluid tank 160 may not be evenly pressed directly by the injector. Therefore, a pressure plate 190 made of a material harder than the fluid tank 160 can be brought into contact with the lower plate of the fluid tank 160 to evenly press the fluid tank 160.

The pressure plate 190 may further include a hole 191 into which the receiving portion 162 of the fluid tank 160 is inserted. The pressure plate 190 may also prevent the fluid tank 160 from being damaged.

An overall assembled state of the apparatus will be described with reference to FIGS. 3 and 4. The needle unit 170, the cap member 180, the piston 140, the fluid tank 160 and the pressure plate 190 are disposed within the cylinder 110 in this order.

More specifically, the piston 140 has a hollow portion 141 formed in the direction, and the cap member 180 is fitted into the hollow portion 141. The hollow portion 141 of the piston 140 is generally in the shape of a truncated cone with a diameter decreased toward a side opposite to the nozzle 111. The cap member 180 is configured such that a portion thereof which is in contact with the piston 140 corresponds to an internal shape of the hollow portion 141 of the piston 140.

At this time, the bellows 181 of the cap member 180 is disposed within the piston 140 and is larger than the diameter of the hollow portion 141 to prevent the cap member 180 from being inadvertently detached from the piston 140.

The nozzle cap 171 of the needle unit 170 is inserted/press-fitted into the cap member 180. An external shape of the nozzle cap 171 corresponds to an internal shape of the cap member 180. Therefore, the nozzle cap 171 is not inadvertently detached from the cap member 180 due to a frictional force between the nozzle cap 171 and the cap member 180 or an elastic force between the cap member 180 and the nozzle cap 171.

The needle 172 is located within the bellows 181 of the cap member 180 and does not protrude out of the cap member 180.

The fluid tank 160 is disposed within the piston 140, wherein the upper plate of the fluid tank is disposed to face the needle 172 and the bellows 161 is disposed to face an inner circumference surface of the piston 140. The pressure plate 190 is installed at the piston 140 or secured to the fluid tank 160.

Accordingly, the needle unit 170, the cap member 180, the fluid tank 160 and the pressure plate 190 are moved together with the piston 140 in the cylinder 110.

Hereinafter, the injector will be described only by way of example with reference to FIGS. 1, 2 and 5 to 8. In this embodiment, the injector as a gas generator includes the gas-generating unit 130, an internal pressure-adjusting member 136 and the like (see portion "A" in FIG. 2).

The internal pressure-adjusting member 136 is provided at the gas-generating unit 130 to face toward the inside of the gas-supplied space 116 of the cylinder 110 (see FIG. 1). This internal pressure-adjusting member 136 has an internal connection passage 220 for connecting an external air entrance 135 formed at one side of the body part 131 of the gas-generating unit 130 to the gas-supplied space 116, and a shut-off valve 320 which is hermetically moveable in the internal connection passage 220 and divides the internal connection passage 220 into an external air inflow space 222 into which external air can flow from the external air entrance 135 and a generated-gas inflow space 224 into which the gas from the gas-generating unit 130 flows. In addition, the external air entrance 135 is connected to the internal connection passage 220 through an air inflow passage 200.

In the liquid medicine injection apparatus 1000 according to the embodiment of the present invention, when the liquid medicine storage space is filled with the liquid medicine prior to the generation of the gas in the gas-generating unit 130, the shut-off valve 320 is positioned at a location where external air from the external air entrance 135 is caused to flow into the external air inflow space 222 and the external air inflow space 222 is in communication with the gas-supplied space 116, thereby equilibrating the internal pressure of the gas-supplied space 116 to an atmospheric pressure. Therefore, when the operation of filling the liquid medicine storage space 114 of the cylinder 110 with the liquid medicine is performed as preparation for injection of the liquid medicine into the patient's body, the piston 140 separating the liquid medicine storage space 114 from the gas-supplied space 116 minimizes its pushing action interrupting a flow of the liquid medicine introduced into the liquid medicine storage space 114, i.e., a liquid medicine inflow resistance due to the piston 140, thereby facilitating the filling of the liquid medicine storage space with the liquid medicine.

Meanwhile, in the liquid medicine injection apparatus 1000 according to the embodiment of the present invention, when the liquid medicine is injected into the patient's body after the gas is generated in the gas-generating unit 130, the shut-off valve 320 is moved toward the external air inflow space 222 by a propulsive force of the gas flowing from the gas-generating unit 130 into the generated-gas inflow space 224, thereby blocking inflow of external air from the external air entrance 135 into the external air inflow space 222.

Therefore, a high pressure of the gas generated by the gas-generating unit 130 is exerted on the piston 140 in the gas-supplied space 116 so that the piston 140 may be efficiently moved forward and the liquid medicine stored in the liquid medicine storage space 114 may be stably and continuously injected into the patient's body at a constant flow rate.

The shut-off valve 320 may have a front end 322 facing toward the external air inflow space 222, and a body part 324 hermetically movable along a guide wall 242 of the internal connection passage 220, and may be formed with a through passage 327 extending from a through hole 326 of the front end 322 to a through hole 328 formed in a side surface of the body part 324. A through hole 240 for communicating the internal connection passage 220 with the gas-supplied space 116 may be formed in the guide wall 242 of the internal connection passage 220.

When the liquid medicine storage space is filled with the liquid medicine before the gas is generated in the gas-generating unit, the through hole 328 formed in the side surface of the body part 324 of the shut-off valve is fixed at a position where the through hole 328 is aligned with the through hole 240 of the internal connection passage. Therefore, external air introduced into the external air inflow space 222 flows through the through hole 326 of the front end 322, the through passage 327 and the through hole 328 of the body part 324 of the shut-off valve, and flows into the gas-supplied space 116 through the through hole 240 of the internal connection passage, which is aligned with the through hole 328 of the body part 324.

In this state, the internal pressure of the gas-supplied space 116 is equilibrated to the atmospheric pressure, and the liquid medicine inflow resistance, caused by the piston 140 when the operation of filling the liquid medicine storage space 114 with the liquid medicine is performed, is reduced, thereby facilitating the filling of the liquid medicine storage space with the liquid medicine.

In addition, an end of the external air inflow space 222 of the internal connection passage 220 may be opened and a sealing member 380 may be further included to seal this opened end. The sealing member 380 may be composed of a stepped sealing cap 382 and a rubber packing member 384 that is fitted into and coupled with a concave receiving portion 382*a* of such sealing cap. A tension spring 360 and the shut-off valve 320 are sequentially housed in the internal connection passage 220 through the opened end. A stepped portion 382*b* of the sealing cap is inserted into and tightly coupled with the opened end of the external air inflow space 222, and the rubber packing member 384 faces the external air inflow space 222.

When the liquid medicine is injected after the gas is generated in the gas-generating unit, the gas generated in the gas-generating unit flows into the generated-gas inflow space 224 through a gas-flowing passage 260, which connects the body part 131 of the gas-generating unit 130 and the generated-gas inflow space 224, so as to push a rear portion of the body part 324 of the shut-off valve 320. The shut-off valve 320 is moved toward the external air inflow space 222 so that the front end 322 of the shut-off valve 320 is brought into contact with the sealing member 380 (See FIG. 8). This configuration prevents external air from the external air entrance 135 and the air inflow passage 200 from flowing into the through passage 327 of the shut-off valve 320 via the through hole 326 formed on the front end 322 of the shut-off valve 320. In particular, when the front end 322 of the shut-off valve 320 presses and is in contact with the rubber packing member 384 constituting the sealing member 380, the front end 322 of the shut-off valve 320 is in close contact with the rubber packing member 384 and is blocked so that it is possible to reliably prevent external air from leaking via the through hole 326 formed on the front end 322 of the shut-off valve 320. In this state, a high pressure of the gas generated by the gas-generating unit 130 is exerted on the piston 140, so that the piston 140 can be effectively moved forward and it is possible to stably and continuously inject the liquid medicine accommodated in the liquid medicine storage space 114 into the patient's body at a constant flow rate.

Moreover, a plurality of ring-shaped protrusions, preferably at least two, and more preferably four ring-shaped protrusions 3240*a*, 3240*b*, 3240*c* and 3240*d* may be formed on a circumference of the body part 324 of the shut-off valve 320. At least one protrusion 3240*c* of the ring-shaped protrusions is in close contact with a gentle stepped portion 1362 formed on the guide wall 242 of the internal connection passage 220. Accordingly, before the gas generated in the gas-generating unit 130 is introduced into the generated-gas inflow space 224, it is possible to securely fix the shut-off valve 320 at a location where the through hole 328 formed in the side surface of the body part 324 of the shut-off valve 320 is aligned with the through hole 240 of the internal connection passage (see FIG. 7). Meanwhile, when the gas generated in the gas-generating unit 130 is introduced into the generated-gas inflow space 224, the pressure of the introduced gas is exerted on a rear portion of the body part 324 of the shut-off valve 320 so that the shut-off valve 320 may overcome an obstacle to a movement, which is caused by engagement of the ring-shaped protrusion 3240*c* with the stepped portion 1362, and be moved toward the external air inflow space 222 (see FIG. 8).

In other words, with the aforementioned configuration, it is possible to prevent the shut-off valve 320 from being moved due to temporary external impact or external air, so that the internal pressure of the gas-supplied space 116 is stably equilibrated to the atmospheric pressure before the gas is generated in the gas-generating unit, whereas upon generation of the gas in the gas-generating unit, the gas pressure generated in response to a liquid medicine injection mode enables the shut-off valve 320 to overcome an obstacle to a movement, which is caused by the stepped portion 1362, and to be moved toward the external air inflow space 222, and the front end 322 of the shut-off valve 320 is in close contact with the sealing member 380 to block the inflow of external air.

Further, each of sealing rings 340*a* or 340*b* can be inserted between the pair of two ring-shaped protrusions 3240*a* and 3240*b* or 3240*c* and 3240*d*. The sealing rings 340*a* and 340*b* allow the shut-off valve 320 to be hermetically moved along the guide wall 242 of the internal connection passage 220. In addition, the liquid medicine injection apparatus 1000 of the embodiment of the present invention may further include the tension spring 360 fixedly installed in the generated-gas inflow space 224 and coupled to the body part 324 of the shut-off valve 320.

When the gas is generated in the gas-generating unit, the gas pressure generated in response to the liquid medicine injection mode enables the shut-off valve 320 to overcome the elastic restoring force caused by the tension spring 360 and to be moved toward the external air inflow space 222, and the front end 322 of the shut-off valve 320 is in close contact with the sealing member 380 to block the inflow of external air. Moreover, the tension spring 360 prevents the shut-off valve 320 from being moved due to temporary external impact or external air by means of the elastic restoring force, thereby assisting in attaining a stable equilibrium between the internal pressure of the gas-supplied space 116 and the atmospheric pressure before the gas is generated in the gas-generating unit. In addition, when the generation of the gas is completed, the elastic restoring force of the tension spring helps to return the shut-off valve 320 to its original state where the injection of the liquid medicine is not initiated.

Further, the external air entrance 135 may be provided with a gas-permeable/liquid-impermeable hydrophobic filter (not shown). Such hydrophobic filter allows external air to flow into the apparatus through the external air entrance 135, but prevents water, a liquid medicine, a liquid contaminant and the like from flowing into the apparatus from the outside. As for the hydrophobic filter, those disclosed in prior arts or known in the art may be employed.

Meanwhile, most of the elements constituting the liquid medicine injection apparatus 1000 according to the embodiment of the present invention are formed of a material suitable for withstanding external impact and may be formed of a plastic material, a synthetic resin or the like that have been well known in the art. The sealing rings 340*a* and 340*b* and the rubber packing member 384 may be formed of a known elastic rubber material. Furthermore, plastic or spring steel may be used as a material for the tension spring 360. However, it will be readily understood by those skilled in the art that the present invention is not limited thereto and the aforementioned elements may be formed of various materials well known in the art, wherein the materials meet the object of the present invention, satisfy biocompatibility, are less corroded and have predetermined durability.

Meanwhile, a process of successively injecting a second liquid medicine after completion of injection of a first liquid medicine, or a flushing process using an additional fluid after completion of injection of a first liquid medicine will be described with reference to FIGS. 9A to 9E.

Figure 9A:
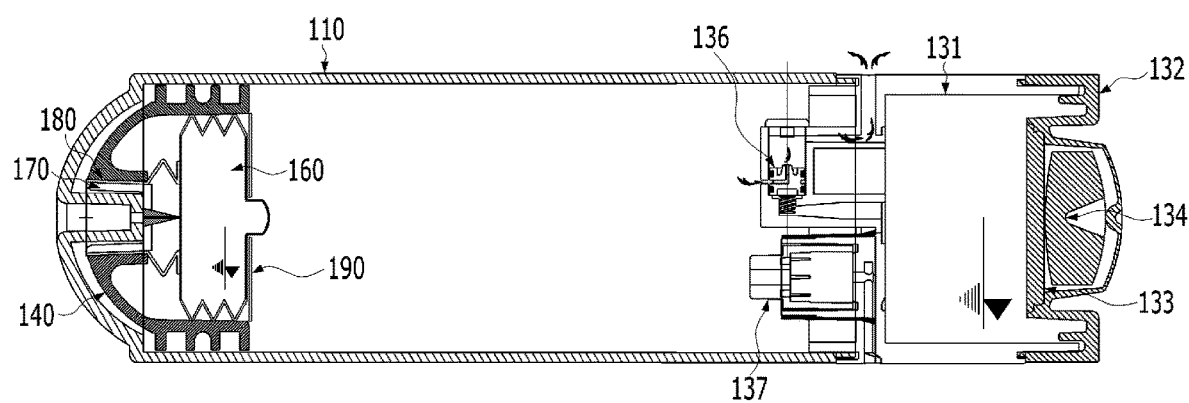
FIGS. 9A to 9E are views of usage states, schematically illustrating operations of liquid medicine injection apparatuses capable of injecting an additional fluid after completion of injection of a liquid medicine according to embodiments of the present invention.

FIG. 9A schematically illustrates a state before the liquid medicine injection apparatus 1000 is filled with the liquid medicine. The piston 140 is coupled to the needle 170, the cap member 180, the fluid tank 160 and the pressure plate 190 as described above and is disposed adjacent to the nozzle 111. At this time, the nozzle 111 is placed within the nozzle cap 171 of the needle unit 170.

Then, the piston 140 is moved toward the gas-generating unit 130 as the liquid medicine storage space is filled with the liquid medicine. Of course, the needle unit 170, the cap member 180, the fluid tank 160 and the pressure plate 190 coupled to the piston 140 are also moved together.

At this time, the cap member 180 is not pressed under the predetermined pressure. Specifically, even when the pressure in the liquid medicine storage space 114 is increased, the pressure in the gas-supplied space 116 is low and the piston 140 is moved toward the gas-supplied space 116, so that the cap member 180 is not pressed by the pressure at which the cap member is deformed (the predetermined pressure). Further, since the fluid tank 160 is in a sealed state, it is not deformed by the pressure.

Figure 9B:
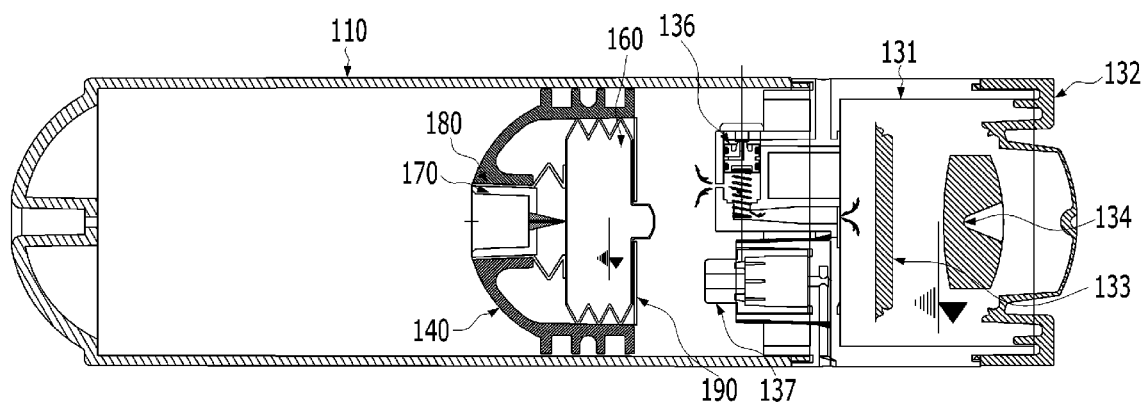

Referring to FIG. 9B, when the filling of the liquid medicine storage space with the liquid medicine is completed, the partition wall 133 is removed to fall the solid material 134 into the liquid material so that the solid material and the liquid material are reacted with each other to generate the gas. As the pressure in the gas-supplied space 116 is increased by the generated gas, the piston 140 is moved toward the nozzle to inject the liquid medicine in the liquid medicine storage space 114 into the patient's body.

Even though the gas is continuously generated until the injection of the liquid medicine is completed, the cap member 180 is subjected to a pressure lower than the pressure at which the cap member is deformed (the predetermined pressure). In other words, the bellows 181 of the cap member 180 is not pressed by the fluid tank 160. Since the needle 172 does not penetrate the fluid tank 160, the fluid tank 160 keeps its outer shape even though it is subjected to the pressure.

Figure 9C:
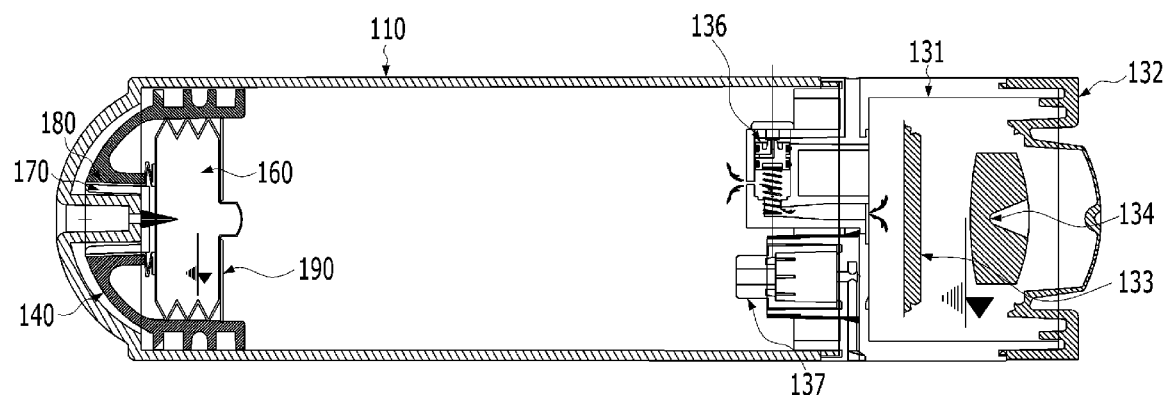

As shown in FIG. 9C, when the injection of the liquid medicine into the patient's body is completed, a predetermined pressure corresponding to an excess pressure, by which a pressure in the gas-supplied space 116 exceeds a pressure in the liquid medicine storage space 114, is produced. This predetermined pressure deforms the cap member 180. That is, the cap member 180 is pressed under the predetermined pressure, and the bellows 181 of the cap member 180 is pressed by the fluid tank 160.

As the bellows 181 of the cap member 180 is pressed, the needle 172 is exposed to the outside of the cap member 180 and penetrates the fluid tank 160. Then, the fluid (a second liquid medicine or a saline solution) stored in the fluid tank 160 flows out through the needle 172. At this time, the pressure plate 190 can evenly transmit the pressure of the gas to the fluid tank 160.

Figure 9D:
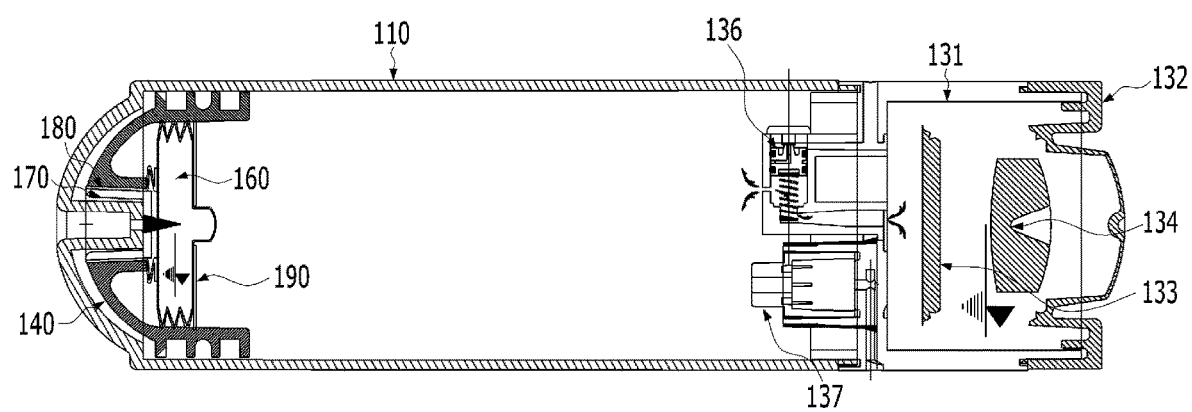

Next, FIG. 9D illustrates a process of causing the fluid tank 160 to be compressed by the pressure of the gas. As the fluid tank 160 is compressed, the fluid (a second liquid medicine or a saline solution) continuously flows into the nozzle 111 through the needle 172. Therefore, for example, when two kinds of liquid medicines are sequentially administered to a patient according to combination chemotherapy, the second liquid medicine in the fluid tank 160 is successively injected after completion of the injection of the first liquid medicine in the liquid medicine storage space 114. Meanwhile, in a case where a flushing fluid, for example, a saline solution, is contained in the fluid tank 160, the saline solution flushes the nozzle 111 and/or a tube (not shown) inserted into the nozzle 111 to wash away the liquid medicine remaining in the nozzle and/or the tube and inject it into the patient's body.

Figure 9E:
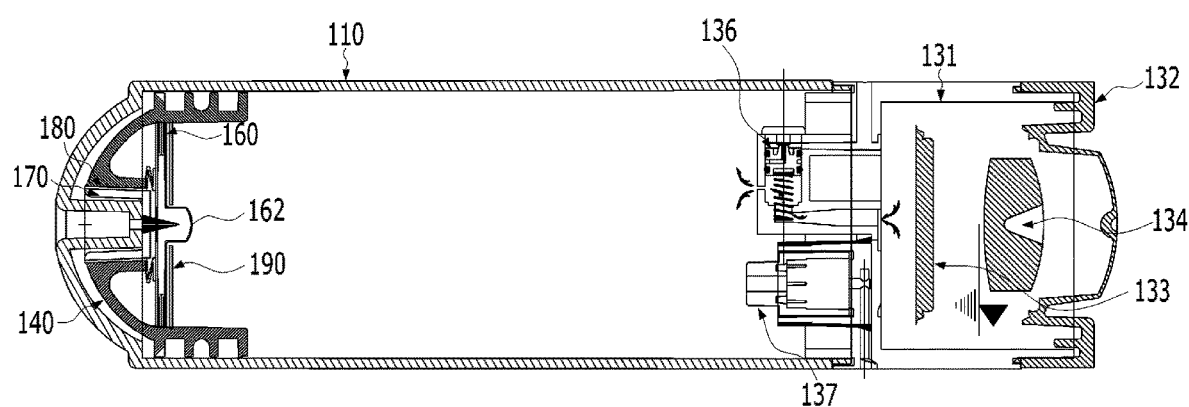

As shown in FIG. 9E, when the fluid tank 160 is completely compressed by the pressure of the gas, an end of the needle 172 is disposed in the receiving portion 162 of the fluid tank 160. Thus, the receiving portion 162 enables the needle 172 to supply the fluid (a second liquid medicine or a saline solution) without being clogged until the fluid tank 160 is fully compressed. At this time, the amount of the second liquid medicine injected into the patient's body is a dose required according to a therapeutic regimen. The amount of the saline solution is an amount that does not adversely affect patient health when it is injected into the patient's body and is sufficient to wash away the liquid medicine remaining in the nozzle and/or the tube.

In a case where the fluid in the fluid tank 160 is the second liquid medicine, the second liquid medicine can be successively injected after completion of the injection of the first liquid medicine by means of the aforementioned operation by using a single apparatus.

Alternatively, when the fluid in the fluid tank 160 is the saline solution, it is possible to effectively wash away the residual liquid medicine in the liquid medicine injection apparatus and/or in the tube, whereby the liquid medicine such as anticancer drugs or analgesics containing a narcotic component does not remain. Therefore, the apparatus of the present invention can solve problems due to the residual liquid medicine in the liquid medicine injection apparatus and/or in the tube, for example, environmental problems and illegal distribution of dangerous drugs.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

I claim:

1. A liquid medicine injection apparatus capable of injecting an additional fluid after completion of injection of a liquid medicine, comprising:

a cylinder elongated in a direction and having a nozzle formed at one end of the cylinder;

a piston installed to be hermetically movable within the cylinder in the direction, wherein the piston defines a liquid medicine storage space to be filled with the liquid medicine introduced through the nozzle;

an injector provided at a second end of the cylinder to allow the piston to be moved forward;

a fluid tank for storing a fluid in a sealed state, wherein the fluid tank is disposed in the cylinder so as to be movable together with the piston and is deformable by a pressure;

a needle unit disposed between the nozzle and the fluid tank, wherein the needle unit can penetrate a portion of the fluid tank to communicate the nozzle with the fluid tank; and a cap member disposed between the needle unit and the fluid tank, wherein before the injection of the liquid medicine with which the liquid medicine storage space is filled is completed, the cap member maintains its shape, whereas after the injection of the liquid medicine with which the liquid medicine storage space is filled is completed, the cap member is deformed to allow the needle unit to penetrate the fluid tank.

2. The liquid medicine injection apparatus of claim 1, wherein the fluid tank is installed within the piston.

3. The liquid medicine injection apparatus of claim 2, further comprising a pressure plate installed to be movable in the piston, wherein the pressure plate is brought into contact with the fluid tank to cause an internal space of the piston with the fluid tank installed therein to be separated from an external space.

4. The liquid medicine injection apparatus of claim 3, wherein a portion of the fluid tank placed radially with respect to the direction is formed of a bellows.

5. The liquid medicine injection apparatus of claim 3, wherein the needle unit comprises:

a nozzle cap for surrounding the nozzle formed to extend into the liquid medicine storage space; and a needle secured to the nozzle cap.

6. The liquid medicine injection apparatus of claim 5, wherein the cap member can surround the nozzle cap, and a portion of the cap member placed radially with respect to the direction and adjacent to the needle is formed of a bellows.

7. The liquid medicine injection apparatus of claim 3, wherein the injector comprises a gas generator for generating a gas to press the piston.

8. The liquid medicine injection apparatus of claim 3, wherein the fluid is a liquid medicine different from the liquid medicine with which the liquid medicine storage space is filled, or a saline solution.

9. The liquid medicine injection apparatus of claim 1, wherein a portion of the fluid tank placed radially with respect to the direction is formed of a bellows.

10. The liquid medicine injection apparatus of claim 1, wherein the needle unit comprises:

a nozzle cap for surrounding the nozzle formed to extend into the liquid medicine storage space; and a needle secured to the nozzle cap.

11. The liquid medicine injection apparatus of claim 10, wherein the cap member can surround the nozzle cap, and a portion of the cap member placed radially with respect to the direction and adjacent to the needle is formed of a bellows.

12. The liquid medicine injection apparatus of claim 1, wherein the injector comprises a gas generator for generating a gas to press the piston.

13. The liquid medicine injection apparatus of claim 1, wherein the fluid is a liquid medicine different from the liquid medicine with which the liquid medicine storage space is filled, or a saline solution.

* * * * *